United States Patent
Maase et al.

(10) Patent No.: US 7,501,522 B2
(45) Date of Patent: Mar. 10, 2009

(54) METHOD FOR THE PRODUCTION OF PURIFIED 1,3-SUBSTITUTED IMIDAZOLIUM SALTS

(75) Inventors: Matthias Maase, Speyer (DE); Klemens Massonne, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 550 days.

(21) Appl. No.: 10/564,871

(22) PCT Filed: Jun. 30, 2004

(86) PCT No.: PCT/EP2004/007076

§ 371 (c)(1), (2), (4) Date: Feb. 6, 2006

(87) PCT Pub. No.: WO2005/019183

PCT Pub. Date: Mar. 3, 2005

(65) Prior Publication Data

US 2006/0149074 A1    Jul. 6, 2006

(30) Foreign Application Priority Data

Jul. 21, 2003    (DE) ................ 103 33 239

(51) Int. Cl.
C07F 9/80    (2006.01)
C07F 5/02    (2006.01)

(52) U.S. Cl. ............... 548/102; 548/107; 548/110

(58) Field of Classification Search ............. 548/102
See application file for complete search history.

(56) References Cited

U.S. PATENT DOCUMENTS 6,939,974 B2 * 9/2005 Earle et al. ............. 548/347.1

FOREIGN PATENT DOCUMENTS

| EP | 1 182 196 | 2/2002 |
|---|---|---|
| WO | WO-96/18459 | 6/1996 |
| WO | WO-01/40146 | 6/2001 |
| WO | WO-01/77081 | 10/2001 |
| WO | WO-02/34722 | 5/2002 |
| WO | WO-03/013685 | 2/2003 |

OTHER PUBLICATIONS

Arduengo, Anthony J. et al., "Electronic Stabilization of Nucleophilic Carbenes", J. Am. Chem. Soc. 114 (1992), pp. 5530-5534.
Hamill, Jennifer T. et al., "Comment on the Preparation of the Ionic Liquid 1-ethyl-3-methylimidazolium Ethanoate: A Unique Monomeric, Homoleptic Pentacoordinate Lead Ethanoate Complex", Chem. Commun. (2000), pp. 1929-1930.
Dyson, Paul J. et al., "Transition Metal Catalysed Reactions in Room-Temperature Ionic Liquids", Electrochemical Society Proceedings, vol. 99-41, pp. 161-168.
Wasserscheid, Peter et al., "Ionische Flussigkeiten—neue "Losungen" fur de Ubergangsmetallkatalyse", Angew Chem. 112 (2000), pp. 3926-3945.

* cited by examiner

Primary Examiner—Kamal A Saeed
(74) Attorney, Agent, or Firm—Connolly Bove Lodge & Hutz LLP

(57) ABSTRACT

Process for preparing purified 1,3-substituted imidazolium salts of the formula (I)

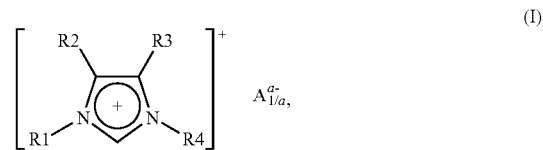

by reacting a 1,3-substituted imidazolium salt of the formula (II),

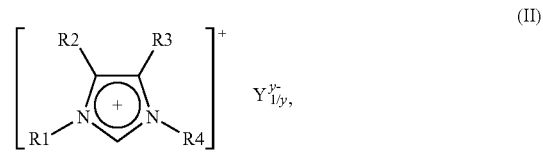

with a strong base at from 20 to 250° C. while distilling off the 1,3-substituted imidazol-2-ylidene formed, in which the 1,3-substituted imidazol-2-ylidene which has been distilled off is brought into contact in the gaseous state with the protic acid $H_aA$ (III) and/or the 1,3-substituted imidazol-2-ylidene which has been distilled off is passed in the gaseous or condensed state into a receiver comprising the protic acid $H_aA$ (III).

14 Claims, No Drawings

METHOD FOR THE PRODUCTION OF PURIFIED 1,3-SUBSTITUTED IMIDAZOLIUM SALTS

RELATED APPLICATIONS

This application is a national stage application (under 35 U.S.C. 371) of PCT/EP2004/007076 filed Jun. 30, 2004 which claims benefit to German application 103 33 239.1 filed Jul. 21, 2003.

The present invention relates to a process for preparing purified 1,3-substituted imidazolium salts of the formula (I)

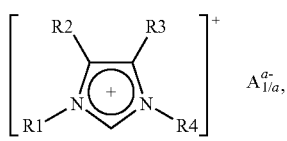

where
the radicals $R^1$, $R^2$, $R^3$ and $R^4$ are each, independently of one another, a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens, where adjacent radicals $R^1$ and $R^2$, $R^2$ and $R^3$ or $R^3$ and $R^4$ may also be joined to one another and the radicals $R^2$ and $R^3$ may each also be, independently of one another, hydrogen, halogen or a functional group;

and
$A^{a-}$ is the partly or fully deprotonated anion of an inorganic or organic protic acid $H_aA$ (III), where a is a positive integer and indicates the charge on the anion, by reacting a 1,3-substituted imidazolium salt of the formula (II),

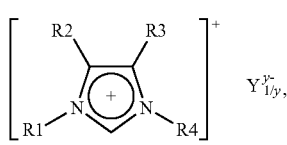

where the radicals $R^1$, $R^2$, $R^3$ and $R^4$ are as defined above and the anion $Y^{y-}$ is the partly or fully deprotonated anion of an inorganic or organic protic acid $H_yY$ (IV), where y is a positive integer and indicates the charge on the anion, with a strong base at from 20 to 250° C. while distilling off the 1,3-substituted imidazol-2-ylidene formed.

1,3-Substituted imidazolium salts belong to the group of ionic liquids and are becoming increasingly important. They represent, for example, good solvents for organic and inorganic compounds in a variety of applications.

Ionic liquids are becoming increasingly important as solvents, for example for carrying out chemical reactions. P. Wasserscheid et al., Angew. Chem. 112 (2000), pages 3926 to 3945, give an overview of the use of these liquids in homogeneous transition metal catalysis. The purity of the ionic liquid used is of great importance here, since impurities generally have an adverse effect on the course of the chemical reactions. Thus, for example, P. Dyson et al. in Electrochemical Society Proceedings, Volume 99-41, pages 161 to 168, refer to problems when using chloride-containing ionic liquids in liquid-phase hydrogenation and in the Suzuki reaction. For this reason, the purity of the desired product has to meet demanding requirements in the preparation of ionic liquids.

An important group of ionic liquids comprises substituted imidazolium salts. In general, these are obtained from the corresponding N-substituted imidazole by alkylation of the second nitrogen.

WO 02/34722 describes two different routes for preparing 1,2,3-substituted, 1,2,3,4-substituted and 1,2,3,4,5-substituted imidazolium salts: (1) In the indirect route, the appropriate substituted imidazole is reacted with an organic halide and the halide ion of the substituted imidazolium halide is replaced by the desired anion by means of ion exchange. (2) In the direct route, the appropriate substituted imidazole is reacted with an alkyl triflate or a trialkyloxonium salt of the desired anion (e.g. triethyloxonium tetrafluoroborate). Disadvantages of the preparation via the indirect route (1) are the high cost of the ion exchange which is subsequently required and the extraction of the product with an organic solvent which may be associated therewith and also the residual content of halide ions which, for example, can have an adverse effect on the reactions catalyzed by transition metals. A disadvantage of the preparation via the direct route (2) is that the alkylating reagent determines both the substituent and the anion and the variation range and flexibility in respect of the anion is thus restricted.

EP-A 1 182 196 teaches the halide-free preparation of 1,3-substituted imidazolium salts by reaction of the parent 1-substituted imidazole with the appropriate organic disulfate as alkylating agent and subsequent ion exchange with a metal salt comprising the desired anion. Thus, for example, 1-butyl-3-methylimidazolium tetrafluoroborate is prepared by reacting 1-butylimidazole with dimethyl sulfate, subsequently treating the intermediate with sodium tetrafluoroborate and extracting the product a number of times with methylene chloride. Although the overall process leads to apparently chloride-free 1,3-substituted imidazolium salts, it has the critical disadvantage of the use of an organic disulfate which, owing to its carcinogenic and corrosive action, represents an increased safety risk and therefore requires a tremendous outlay in terms of safety precautions. Furthermore, ion exchange by addition of a metal salt comprising the desired anion is very costly since the mixture subsequently has to be worked up by extraction with an organic solvent.

WO 01/40146 describes the preparation of 1,3-substituted imidazolium salts by reaction of the parent 1-substituted imidazole with a fluorinated ester, for example a trifluoroacetic ester, or an alkyl sulfonate as alkylating agent in the presence of a solvent. A subsequent reaction of the product obtained with the acid of the desired anion, for example tetrafluoroboric acid or hexafluorophosphoric acid, gives the desired 1,3-substituted imidazolium salt in virtually halide-free and metal-free form. A disadvantage of this process is the contamination of the desired 1,3-substituted imidazolium salt with traces of the compounds used in the synthesis or their reaction products, for example excess alkylating agent, salts of the 1-substituted imidazole used, the solvent used or the 1,3-substituted imidazolium salt of the fluorinated acid anion or the sulfonate.

WO 96/18459 discloses the preparation of halide-free ionic liquids by reaction of a halide of the desired imidazolium, pyridinium or phosphonium cation with a lead salt whose anion represents the desired anion for the ionic liquid and removal of the precipitated lead halide. Disadvantages of the process described are the use of stoichiometric amounts of toxic lead salts and the associated formation of stoichiometric amounts of lead halides to be disposed of and also, in particular, the significant contamination of the product with these lead compounds, as indicated, in particular, by J. T. Hamill et al., Chem. Comm. 2000, pages 1929 to 1930.

A disadvantage of the abovementioned processes for preparing substituted imidazolium salts is the formation of a product contaminated with by-products, which can lead to adverse effects in use of the substituted imidazolium salts.

WO 01/77081 discloses a process in which purified 1,3-substituted imidazolium salts which are contaminated neither with halide ions nor with metal ions can be prepared. The starting material is a 1,3-substituted imidazolium salt which has been prepared, for example, by a conventional route, with the anion being able to be different from the anion desired later. In this process, the 1,3-substituted imidazolium salt is heated in the presence of a strong base, for example an alkoxide, under reduced pressure, with the corresponding 1,3-substituted imidazolium-carbene being formed and distilled off. This is condensed as a pure material in a receiver. The condensed carbene is subsequently reacted with the acid of the desired anion or an alcohol to form the purified 1,3-substituted imidazolium salt. A disadvantage of this process is the fact that, as described in A. J. Arduengo et al., J. Am. Chem. Soc. 114, 1992, pages 5530 to 5534, although carbenes which are not strongly sterically hindered are stable for some days in solution, the pure substance is very unstable. Thus, for example, pure 1,3-dimethylimidazol-2-ylidene decomposes even at low temperatures so as to become brown and form a viscous product. Even though the examples described in WO 01/77081 were able to demonstrate that 1-ethyl-3-methylimidazol-2-ylidene, 1-butyl-3-methylimidazol-2-ylidene, 1-hexyl-3-methylimidazol-2-ylidene and 1-octyl-3-methylimidazol-2-ylidene could be obtained in very small amounts in a bulb tube apparatus and confirmed by NMR spectroscopy, the viscous by-products inevitably formed lead to renewed contamination of the desired 1,3-substituted imidazolium salt. The amount of the viscous by-products increases further as a result of the increased residence time as the size of the production batch increases, so that only a highly contaminated product can be obtained when the process is carried out on an industrial scale. Intensive cooling of the distillation receiver to below 0° C. is very costly and energy-consuming in industry.

It is an object of the present invention to find a process for preparing purified 1,3-substituted imidazolium salts which no longer has the abovementioned disadvantages, has great variability and flexibility in respect of the choice of substituents of the imidazolium cation and the choice of the anion and leads in a technically simple way to pure to highly pure 1,3-substituted imidazolium salts in good yields.

We have found that this object is achieved by a process for preparing purified 1,3-substituted imidazolium salts of the formula (I)

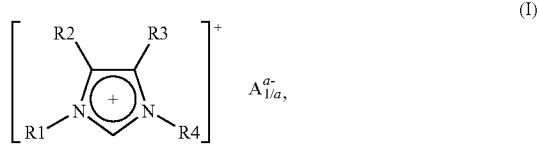

where
the radicals $R^1$, $R^2$, $R^3$ and $R^4$ are each, independently of one another, a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens, where adjacent radicals $R^1$ and $R^2$, $R^2$ and $R^3$ or $R^3$ and $R^4$ may also be joined to one another and the radicals $R^2$ and $R^3$ may each also be, independently of one another, hydrogen, halogen or a functional group;

and
$A^{a-}$ is the partly or fully deprotonated anion of an inorganic or organic protic acid $H_aA$ (III), where a is a positive integer and indicates the charge on the anion, by reacting a 1,3-substituted imidazolium salt of the formula (II),

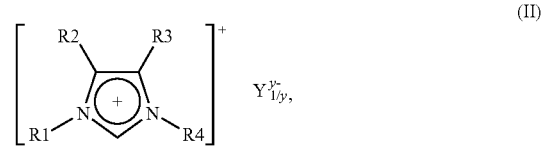

where the radicals $R^1$, $R^2$, $R^3$ and $R^4$ are as defined above and the anion $Y^{y-}$ is the partly or fully deprotonated anion of an inorganic or organic protic acid $H_yY$ (IV), where y is a positive integer and indicates the charge on the anion, with a strong base at from 20 to 250° C. while distilling off the 1,3-substituted imidazol-2-ylidene formed, wherein the 1,3-substituted imidazol-2-ylidene which has been distilled off is brought into contact in the gaseous state with the protic acid $H_aA$ (III) and/or the 1,3-substituted imidazol-2-ylidene which has been distilled off is passed in the gaseous or condensed state into a receiver comprising the protic acid $H_aA$ (III).

The purified 1,3-substituted imidazolium salt (I) which can be prepared by the process of the present invention comprises the 1,3-substituted imidazolium cation of the formula (Ia)

where
the radicals $R^1$, $R^2$, $R^3$ and $R^4$ are each, independently of one another, a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens, where adjacent radicals $R^1$ and $R^2$, $R^2$ and $R^3$ or $R^3$ and $R^4$ may also be joined to one another and the radicals $R^2$ and $R^3$ may each also be, independently of one another, hydrogen, halogen or a functional group.

Possible heteroatoms are in principle all heteroatoms which are able to formally replace a —$CH_2$—, a —CH=, a C≡ or a =C= group. If the carbon-comprising radical comprises heteroatoms, preference is given to oxygen, nitrogen, sulfur, phosphorus and silicon. Preferred groups are, in particular, —O—, —S—, —SO—, —$SO_2$—, —NR—, —N=, —PR—, —$PR_2$ and —$SiR_2$—, where the radical R is the remaining part of the carbon-comprising radical. In the case of $R^2$ and $R^3$, the carbon-comprising radical can also be bound directly via the heteroatom to the imidazolium ring.

Possible functional groups are in principle all functional groups which can be bound to a carbon atom or a heteroatom. Examples of suitable groups are —OH (hydroxy), =O (in particular as a carbonyl group), —NH$_2$ (amino), =NH (imino), —COOH (carboxyl), —CONH$_2$ (carboxamide) and —CN (cyano). Functional groups and heteroatoms can also be directly adjacent, so that combinations of a plurality of adjacent atoms such as —O— (ether), —S— (thioether), —COO— (ester), —CONH— (secondary amide) or —CONR— (tertiary amide) are also encompassed, for example di($C_1$-$C_4$-alkyl)amino, $C_1$-$C_4$-alkyloxy-carbonyl or $C_1$-$C_4$-alkyloxy.

Halogens which may be mentioned are fluorine, chlorine, bromine and iodine.

The process of the present invention is preferably used to prepare purified 1,3-substituted imidazolium salts (I) in which the radicals $R^2$ and $R^3$ are each, independently of one another,
hydrogen;
halogen; or
a functional group;
and the radicals $R^1$, $R^2$, $R^3$ and $R^4$ are each, independently of one another,
$C_1$-$C_{18}$-alkyl which may be substituted by functional groups, aryl, alkyl, aryloxy, alkyloxy, halogen, heteroatoms and/or heterocycles and/or be interrupted by one or more oxygen and/or sulfur atoms and/or one or more substituted or unsubstituted imino groups;
$C_2$-$C_{18}$-alkenyl which may be substituted by functional groups, aryl, alkyl, aryloxy, alkyloxy, halogen, heteroatoms and/or heterocycles and/or be interrupted by one or more oxygen and/or sulfur atoms and/or one or more substituted or unsubstituted imino groups;
$C_6$-$C_{12}$-aryl which may be substituted by functional groups, aryl, alkyl, aryloxy, alkyloxy, halogen, heteroatoms and/or heterocycles;
$C_5$-$C_{12}$-cycloalkyl which may be substituted by functional groups, aryl, alkyl, aryloxy, alkyloxy, halogen, heteroatoms and/or heterocycles;
$C_5$-$C_{12}$-cycloalkenyl which may be substituted by functional groups, aryl, alkyl, aryloxy, alkyloxy, halogen, heteroatoms and/or heterocycles; or
a five- to six-membered oxygen-, nitrogen- and/or sulfur-containing heterocycle which may be substituted by functional groups, aryl, alkyl, aryloxy, alkyloxy, halogen, heteroatoms and/or heterocycles; or
adjacent radicals $R^1$ and $R^2$, $R^2$ and $R^3$ or $R^3$ and $R^4$ together form
an unsaturated, saturated or aromatic ring which may be substituted by functional groups, aryl, alkyl, aryloxy, alkyloxy, halogen, heteroatoms and/or heterocycles and may be interrupted by one or more oxygen and/or sulfur atoms and/or one or more substituted or unsubstituted imino groups.

$C_1$-$C_{18}$-Alkyl which may be substituted by functional groups, aryl, alkyl, aryloxy, alkyloxy, halogen, heteroatoms and/or heterocycles is preferably methyl, ethyl, 1-propyl, 2-propyl, 1-butyl, 2-butyl, 2-methyl-1-propyl(isobutyl), 2-methyl-2-propyl(tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, 2-ethylhexyl, 2,4,4-trimethylpentyl, 1,1,3,3-tetramethylbutyl, 1-nonyl, 1-decyl, 1-undecyl, 1-dodecyl, 1-tridecyl, 1-tetradecyl, 1-pentadecyl, 1-hexadecyl, 1-heptadecyl, 1-octadecyl, cyclopentylmethyl, 2-cyclopentylethyl, 3-cyclopentylpropyl, cyclohexylmethyl, 2-cyclohexylethyl, 3-cyclohexylpropyl, benzyl (phenylmethyl), diphenylmethyl (benzohydryl), triphenylmethyl, 1-phenylethyl, 2-phenylethyl, 3-phenylpropyl, α,α-dimethylbenzyl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonethyl, 2-ethoxycarbonylethyl, 2-butoxycarbonylpropyl, 1,2-di(methoxycarbonyl)ethyl, methoxy, ethoxy, formyl, 1,3-dioxolan-2-yl, 1,3-dioxan-2-yl, 2-methyl-1,3-dioxolan-2-yl, 4-methyl-1,3-dioxolan-2-yl, chloromethyl, 2-chloroethyl, trichloromethyl, trifluoromethyl, 1,1-dimethyl-2-chloroethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl, 6-ethoxyhexyl, acetyl, $C_nF_{2(n-a)+(1-b)}H_{2a+b}$ where $n \leq 30$, $0 \leq a \leq n$ and b=0 or 1 (for example $CF_3$, $C_2F_5$, $CH_2CH_2$—$C_{(n-2)}F_{2(n-2)+1}$, $C_6F_{13}$, $C_8F_{17}$, $C_{10}F_{21}$, $C_{12}F_{25}$), methoxymethyl, 2-methoxyethyl, 2-ethoxyethyl, 2-butoxyethyl, diethoxymethyl, diethoxyethyl, 2-isopropoxyethyl, 2-butoxypropyl, 2-octyloxyethyl, 2-methoxyisopropyl, 2-(methoxycarbonyl)ethyl, 2-(ethoxycarbonyl)ethyl, 2-(n-butoxycarbonyl)ethyl, butylthiomethyl, 2-dodecylthioethyl, 2-phenylthioethyl, 5-hydroxy-3-oxa-pentyl, 8-hydroxy-3,6-dioxaoctyl, 11-hydroxy-3,6,9-trioxaundecyl, 7-hydroxyoxaheptyl, 11-hydroxy-4,8-dioxaundecyl, 15-hydroxy-4,8,12-trioxapentadecyl, 9-hydroxy-5-oxanonyl, 14-hydroxy-5,10-oxatetradecyl, 5-methoxy-3-oxapentyl, 8-methoxy-3,6-dioxaoctyl, 11-methoxy-3,6,9-trioxaundecyl, 7-methoxy-4-oxaheptyl, 11-methoxy-4,8-dioxaundecyl, 15-methoxy-4,8,12-trioxapentadecyl, 9-methoxy-5-oxanonyl, 14-methoxy-5,10-oxatetradecyl, 5-ethoxy-3-oxapentyl, 8-ethoxy-3,6-dioxaoctyl, 11-ethoxy-3,6,9-trioxaundecyl, 7-ethoxy-4-oxaheptyl, 11-ethoxy-4,8-dioxaundecyl, 15-ethoxy-4,8,12-trioxapentadecyl, 9-ethoxy-5-oxanonyl or 14-ethoxy-5,10-oxatetra-decyl.

$C_2$-$C_{18}$-Alkenyl which may be substituted by functional groups, aryl, alkyl, aryloxy, alkyloxy, halogen, heteroatoms and/or heterocycles and/or be interrupted by one or more oxygen and/or sulfur atoms and/or one or more substituted or unsubstituted imino groups is preferably vinyl, 2-propenyl, 3-butenyl, cis-2-butenyl, trans-2-butenyl or $C_nF_{2(n-a)-(1-b)}H_{2a-b}$ where $n \leq 30$, $0 \leq a \leq n$ and b=0 or 1.

$C_6$-$C_{12}$-Aryl which may be substituted by functional groups, aryl, alkyl, aryloxy, alkyloxy, halogen, heteroatoms and/or heterocycles is preferably phenyl, tolyl, xylyl, α-naphthyl, β-naphthyl, 4-diphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2-nitrophenyl, 4-nitrophenyl, 2,4-dinitrophenyl, 2,6-dinitrophenyl, 4-dimethylaminophenyl, 4-acetylphenyl, methoxyethylphenyl, ethoxymethylphenyl, methylthiophenyl, isopropylthiophenyl or tert-butylthiophenyl or $C_6F_{(5-a)}H_a$ where $0 \leq a \leq 5$.

$C_5$-$C_{12}$-Cycloalkyl which may be substituted by functional groups, aryl, alkyl, aryloxy, alkyloxy, halogen, heteroatoms and/or heterocycles is preferably cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl, $C_nF_{2(n-a)-(1-b)}H_{2a-b}$ where $n \leq 30$, $0 \leq a \leq n$ and $b=0$ or 1 or a saturated or unsaturated bicyclic system such as norbornyl or norbornenyl.

$C_5$-$C_{12}$-Cycloalkenyl which may be substituted by functional groups, aryl, alkyl, aryloxy, alkyloxy, halogen, heteroatoms and/or heterocycles is preferably 3-cyclopentenyl, 2-cyclohexenyl, 3-cyclohexenyl, 2,5-cyclohexadienyl or $C_nF_{2(n-a)-3(1-b)}H_{2a-3b}$ where $n \leq 30$, $0 \leq a \leq n$ and $b=0$ or 1.

A five- to six-membered oxygen-, nitrogen- and/or sulfur-containing heterocycle which may be substituted by functional groups, aryl, alkyl, aryloxy, alkyloxy, halogen, heteroatoms and/or heterocycles is preferably furyl, thienyl, pyrryl, pyridyl, indolyl, benzoxazolyl, dioxolyl, dioxyl, benzimidazolyl, benzothiazolyl, dimethylpyridyl, methylquinolyl, dimethylpyrryl, methoxyfuryl, dimethoxypyridyl or difluoropyridyl.

If the adjacent radicals $R^1$ and $R^2$, $R^2$ and $R^3$ or $R^3$ and $R^4$ together form an unsaturated, saturated or aromatic ring which may be substituted by functional groups, aryl, alkyl, aryloxy, alkyloxy, halogen, heteroatoms and/or heterocycles and may be interrupted by one or more oxygen and/or sulfur atoms and/or one or more substituted or unsubstituted imino groups, the two adjacent radicals preferably form a 1,3-propylene, 1,4-butylene, 2-oxa-1,3-propylene, 1-oxa-1,3-propylene, 2-oxa-1,3-propylene, 1-oxa-1,3-propenylene, 1-aza-1,3-propenylene, 1-$C_1$-$C_4$-alkyl-1-aza-1,3-propenylene, 1,4-buta-1,3-dienylene, 1-aza-1,4-buta-1,3-dienylene or 2-aza-1,4-buta-1,3-dienylene moiety.

If the abovementioned radicals comprise oxygen and/or sulfur atoms and/or substituted or unsubstituted imino groups, the number of oxygen and/or sulfur atoms and/or imino groups is not subject to any restrictions. There are generally no more than 5 of them present in the radical, preferably not more than 4 and very particularly preferably not more than 3.

If the abovementioned radicals comprise heteroatoms, there is generally at least one carbon atom, preferably at least two carbon atoms, present between two heteroatoms.

The radicals $R^1$ and $R^4$ are particularly preferably each, independently of one another, unbranched or branched $C_1$-$C_{12}$-alkyl such as methyl, ethyl, 1-propyl, 2-propyl, 1-butyl, 2-butyl, 2-methyl-1-propyl(isobutyl), 2-methyl-2-propyl (tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, 1-heptyl, 1-octyl, 1-nonyl, 1-decyl, 1-undecyl, 1-dodecyl, 1-tetradecyl, 1-hexadecyl, 1-octadecyl, 2-hydroxyethyl, benzyl, 3-phenylpropyl, vinyl, 2-cyanoethyl, 2-(methoxycarbonyl)ethyl, 2-(ethoxycarbonyl)ethyl, 2-(n-butoxycarbonyl)ethyl, dimethylamino, diethylamino, trifluoromethyl, difluoromethyl, fluoromethyl, pentafluoroethyl, heptafluoropropyl, heptafluoroisopropyl, nonafluorobutyl, nonafluoroisobutyl, undecylfluoropentyl, undecylfluoroisopentyl or 6-hydroxyhexyl or propylsulfonic acid.

The radicals $R^2$ and $R^3$ are particularly preferably each, independently of one another, hydrogen or unbranched or branched $C_1$-$C_{12}$-alkyl such as methyl, ethyl, 1-propyl, 2-propyl, 1-butyl, 2-butyl, 2-methyl-1-propyl(isobutyl), 2-methyl-2-propyl(tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, nonyl, decyl, undecyl, dodecyl, 2-hydroxyethyl, 2-cyanoethyl, 2-(methoxycarbonyl)ethyl, 2-(ethoxycarbonyl)ethyl, 2-(n-butoxycarbonyl)ethyl, dimethylamino, diethylamino, chlorine, trifluoromethyl, difluoromethyl, fluoromethyl, pentafluoroethyl, heptafluoropropyl, heptafluoroisopropyl, nonafluorobutyl, nonafluoroisobutyl, undecylfluoropentyl, undecylfluoroisopentyl or 6-hydroxyhexyl.

The process of the present invention is very particularly preferably used to prepare a purified 1,3-substituted imidazolium salt (I) in which the radicals $R^1$ and $R^4$ are each, independently of one another, methyl, ethyl, 1-propyl, 2-propyl, 1-butyl, 1-pentyl, 1-hexyl, 1-heptyl, 1-octyl, 1-nonyl, 1-decyl, 1-dodecyl, 1-tetradecyl, 1-hexadecyl, 1-octadecyl, 1-(2-ethyl)hexyl, benzyl, 3-phenylpropyl, 6-hydroxyhexyl or phenyl and the radicals $R^2$ and $R^3$ are each, independently of one another, hydrogen, methyl, ethyl, n-propyl, 2-propyl, 1-butyl, 1-hexyl, 6-hydroxyhexyl, phenyl or chlorine.

The process of the present invention is very particularly preferably used for preparing a purified 1,3-substituted imidazolium salt (I) whose 1,3-substituted imidazolium cation is 1,3-dimethylimidazolium, 1-ethyl-3-methylimidazolium, 1-methyl-3-propylimidazolium, 1-isopropyl-3-methylimidazolium, 1-butyl-3-methylimidazolium, 1-methyl-3-pentylimidazolium, 1-hexyl-3-methylimidazolium, 1-heptyl-3-methylimidazolium, 1-methyl-3-octylimidazolium, 1-decyl-3-methylimidazolium, 1-methyl-3-benzyl-imidazolium, 1-methyl-3-(3-phenylpropyl)imidazolium, 1-(2-ethyl)hexyl-3-methyl-imidazolium, 1-methyl-3-nonylimidazolium, 1-methyl-3-decylimidazolium, 1,2,3-trimethylimidazolium, 1-ethyl-2,3-dimethylimidazolium or 1-butyl-2,3-dimethylimidazolium.

The purified 1,3-substituted imidazolium salt (I) which can be prepared by the process of the present invention comprises the anion $A^{a-}$ which is the partly or fully deprotonated anion of an inorganic or organic protic acid $H_aA$ (III), where a is a positive integer and indicates the charge on the anion.

For the purposes of the present invention, a partly deprotonated anion is an anion of a polybasic acid which still comprises one or more deprotonatable hydrogen atoms. Correspondingly, a fully deprotonated anion is an anion which comprises no further deprotonatable hydrogen atoms.

The process of the present invention is preferably used for preparing purified 1,3-substituted imidazolium salts (I) in which the anion $A^{a-}$ is fluoride; hexafluorophosphate; hexafluoroarsenate; hexafluoroantimonate; trifluoroarsenate; nitrite; nitrate; sulfate; hydrogensulfate; carbonate; hydrogencarbonate; phosphate; hydrogenphosphate; dihydrogenphosphate; vinyl phosphonate; dicyanamide; bis(pentafluoroethyl)phosphinate; tris(pentafluoroethyl)trifluorophosphate; tris(heptafluoropropyl)trifluorophosphate; bis[oxalato(2-)]borate; bis[salicylato(2-)]borate; bis[1,2-benzenediolato(2-)O,O']borate; tetracyanoborate; tetracarbonylcobaltate;

tetrasubstituted borate of the formula (Va) $[BR^aR^bR^cR^d]^-$, where $R^a$ to $R^d$ are each, independently of one another, fluorine or a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens;

organic sulfonate of the formula (Vb) $[R^e\text{---}SO_3]^-$, where $R^e$ is a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens;

carboxylate of the formula (Vc) $[R^f\text{---}COO]^-$, where $R^f$ is hydrogen or a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens;

(fluoroalkyl)fluorophosphates of the formula (Vd) $[PF_x(C_yF_{2y+1-z}H_z)_{6-x}]^-$, where $1 \leq x \leq 6$, $1 \leq y \leq 8$ and $0 \leq z \leq 2y+1$;

imide of the formula (Ve) $[R^g\text{---}SO_2\text{---}N\text{---}SO_2\text{---}R^h]^-$, (Vf) $[R^i\text{---}SO_2\text{---}N\text{---}CO\text{---}R^j]^-$ or (Vg) $[R^k\text{---}CO\text{---}N\text{---}CO\text{---}R^l]^-$, where $R^g$ to $R^l$ are each, independently of one another, hydrogen or a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens;

methide of the formula (Vh)

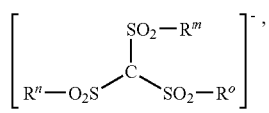

(Vh)

where $R^m$ to $R^o$ are each, independently of one another, hydrogen or a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens;

organic sulfate of the formula (Vi) $[R^pO\text{---}SO_3]^-$, where $R^p$ is a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens; or halometalate of the formula (Vj) $[M_qHal_r]^{s-}$, where M is a metal and Hal is fluorine, chlorine, bromine or iodine, q and r are positive integers and indicate the stoichiometry of the complex and s is a positive integer and indicates the charge on the complex.

The charge "a−" on the anion $A^{a-}$ is "1−", "2−" or "3−". Examples of doubly negatively charged anions are sulfate, hydrogenphosphate and carbonate. An example of a triply negatively charged anion is phosphate.

Possible heteroatoms are in principle all heteroatoms which are able formally to replace a —$CH_2$—, a —CH=, a C≡, or a =C= group. If the carbon-comprising radical comprises heteroatoms, preference is given to oxygen, nitrogen, sulfur, phosphorus and silicon. Particularly preferred groups are —O—, —S—, —SO—, —$SO_2$—, —NR—, —N=, —PR—, —$PR_2$ and —$SiR_2$—, where the radicals R are in each case the remaining part of the carbon-comprising radical.

Possible functional groups are in principle all functional groups which can be bound to a carbon atom or a heteroatom. Examples of suitable groups are —OH (hydroxyl), =O (especially as a carbonyl group), —$NH_2$ (amino), =NH (imino), —COOH (carboxyl), —$CONH_2$ (carboxamide) and —CN (cyano). Functional groups and heteroatoms can also be directly adjacent, so that combinations of a plurality of adjacent atoms such as —O— (ether), —S— (thioether), —COO— (ester), —CONH— (secondary amide) or —CONR— (tertiary amide) are also included.

Halogens which may be mentioned are fluorine, chlorine, bromine and iodine.

Carbon-comprising organic, saturated or unsaturated, acyclic or cyclic, aliphatic, aromatic or araliphatic radicals having from 1 to 30 carbon atoms which serve as radicals $R^a$ to $R^d$ in tetrasubstituted borate (Va), the radical $R^e$ in organic sulfonate (Vb), the radical $R^f$ in carboxylate (Vc) and the radicals $R^g$ to $R^l$ in the imides (Ve), (Vf) and (Vg) are preferably, independently of one another, $C_1$-$C_{30}$-alkyl and their aryl-, heteroaryl-, cycloalkyl-, halogen-, hydroxy-, amino-, carboxy-, formyl-, —O—, —CO—, —CO—O— or —CO—N<-substituted derivatives, for example methyl, ethyl, 1-propyl, 2-propyl, 1-butyl, 2-butyl, 2-methyl-1-propyl(isobutyl), 2-methyl-2-propyl(tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, triacontyl, phenylmethyl(benzyl), diphenylmethyl, triphenylmethyl, 2-phenylethyl, 3-phenylpropyl, cyclopentylmethyl, 2-cyclopentylethyl, 3-cyclopentylpropyl, cyclohexylmethyl, 2-cyclohexylethyl, 3-cyclohexylpropyl, methoxy, ethoxy, formyl, acetyl or $C_nF_{2(n-a)+(1-b)}H_{2a+b}$ where $n \leq 30$, $0 \leq a \leq n$ and b=0 or 1 (for example $CF_3$, $C_2F_5$, $CH_2CH_2\text{---}C_{(n-2)}F_{2(n-2)+1}$, $C_6F_{13}$, $C_8F_{17}$, $C_{10}F_{21}$, $C_{12}F_{25}$);

$C_3$-$C_{12}$-cycloalkyl and their aryl-, heteroaryl-, cycloalkyl-, halogen-, hydroxy-, amino-, carboxy-, formyl-, —O—, —CO— or —CO—O-substituted derivatives, for example cyclopentyl, 2-methyl-1-cyclopentyl, 3-methyl-1-cyclopentyl, cyclohexyl, 2-methyl-1-cyclohexyl, 3-methyl-1-cyclohexyl, 4-methyl-1-cyclohexyl or $C_nF_{2(n-a)-(1-b)}H_{2a-b}$ where $n \leq 30$, $0 \leq a \leq n$ and b=0 or 1;

$C_2$-$C_{30}$-alkenyl and their aryl-, heteroaryl-, cycloalkyl-, halogen-, hydroxy-, amino-, carboxy-, formyl-, —O—, —CO— or —CO—O-substituted derivatives, for example 2-propenyl, 3-butenyl, cis-2-butenyl, trans-2-butenyl or $C_nF_{2(n-a)-(1-b)}H_{2a-b}$ where $n \leq 30$, $0 \leq a \leq n$ and b=0 or 1;

$C_3$-$C_{12}$-cycloalkenyl and their aryl-, heteroaryl-, cycloalkyl-, halogen-, hydroxy-, amino-, carboxy-, formyl-, —O—, —CO— or —CO—O-substituted derivatives, for example 3-cyclopentenyl, 2-cyclohexenyl, 3-cyclohexenyl, 2,5-cyclohexadienyl or $C_nF_{2(n-a)-3(1-b)}H_{2a-3b}$ where $n \leq 30$, $0 \leq a \leq n$ and b=0 or 1; and aryl or heteroaryl having from 2 to 30 carbon atoms and their alkyl-, aryl-, heteroaryl-, cycloalkyl-, halogen-, hydroxy-, amino-, carboxy-, formyl-, —O—, —CO— or —CO—O-substituted components, for example phenyl, 2-methylphenyl(2-tolyl), 3-methylphenyl(3-tolyl), 4-methylphenyl, 2-ethylphenyl, 3-ethylphenyl, 4-ethylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 4-phenylphenyl, 1-naphthyl, 2-naphthyl, 1-pyrrolyl, 2-pyrrolyl, 3-pyrrolyl, 2-pyridinyl, 3-pyridinyl, 4-pyridinyl or $C_6F_{(5-a)}H_a$ where $0 \leq a \leq 5$.

If the anion $A^{a-}$ is a tetrasubstituted borate (Va) $[BR^aR^bR^cR^d]^-$, preference is given to all four radicals $R^a$ to $R^d$ being identical and preferably being fluorine, trifluoromethyl, pentafluoroethyl, phenyl, 3,5-bis(trifluoromethyl)phenyl. Particularly preferred tetrasubstituted borates (Va) are tetrafluoroborate, tetraphenylborate and tetra[3,5-bis(trifluoromethyl)phenyl]borate.

If the anion $A^{a-}$ is an organic sulfonate (Vb) $[R^e—SO_3]^-$, the radical $R^e$ is preferably methyl, trifluoromethyl, pentafluoroethyl, p-tolyl or $C_9F_{19}$. Particularly preferred organic sulfonates (Vb) are trifluoromethanesulfonate (triflate), methanesulfonate, p-toluenesulfonate, nonadecafluorononanesulfonate (nonaflate), dimethylene glycol monomethyl ether sulfate and octylsulfate.

If the anion $A^{a-}$ is a carboxylate (Vc) $[R^f—COO]^-$, the radical $R^f$ is preferably hydrogen, trifluoromethyl, pentafluoroethyl, phenyl, hydroxyphenylmethyl, trichloromethyl, dichloromethyl, chloromethyl, trifluoromethyl, difluoromethyl, fluoromethyl, ethenyl(vinyl), 2-propenyl, —CH=CH—COO$^-$, cis-8-heptadecenyl, —CH$_2$—C(OH)(COOH)—CH$_2$—COO$^-$ or unbranched or branched $C_1$-$C_{18}$-alkyl such as methyl, ethyl, 1-propyl, 2-propyl, 1-butyl, 2-butyl, 2-methyl-1-propyl(isobutyl), 2-methyl-2-propyl(tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, nonyl, decyl, undecyl, dodecyl, heptadecyl. Particularly preferred carboxylates (Vc) are formate, acetate, propionate, butyrate, valerate, benzoate, mandelate, trichloroacetate, dichloroacetate, chloroacetate, trifluoroacetate, difluoroacetate, fluoroacetate.

If the anion $A^{a-}$ is a (fluoroalkyl)fluorophosphate (Vd) $[PF_x(C_yF_{2y+1-z}H_z)_{6-x}]^-$, z is preferably 0. Preference is given to (fluoroalkyl)fluorophosphates (Vd) in which z=0, x=3 and $1 \leq y \leq 4$, specifically $[PF_3(CF_3)_3]^-$, $[PF_3(C_2F_5)_3]^-$, $[PF_3(C_3F_7)_3]^-$ and $[PF_3(C_4F_9)_3]^-$.

If the anion $A^{a-}$ is an imide (Ve) $[R^g—SO_2—N—SO_2—R^h]^-$, (Vf) $[R^i—SO_2—N—CO—R^j]^-$ or (Vg) $[R^kCO—N—CO—R^l]^-$, the radicals $R^g$ to $R^l$ are preferably each, independently of one another, trifluoromethyl, pentafluoroethyl, phenyl, trichloromethyl, dichloromethyl, chloromethyl, trifluoromethyl, difluoromethyl, fluoromethyl or unbranched or branched $C_1$-$C_{12}$-alkyl such as methyl, ethyl, 1-propyl, 2-propyl, 1-butyl, 2-butyl, 2-methyl-1-propyl(isobutyl), 2-methyl-2-propyl(tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, nonyl, decyl, undecyl or dodecyl. Particularly preferred imides (Ve), (Vf) and (Vg) are $[F_3C—SO_2—N—SO_2—CF_3]^-$ (bis(trifluoromethylsulfonyl)imide), $[F_5C_2—SO_2—N—SO_2—C_2F_5]^-$ (bis(pentafluoroethylsulfonyl)imide), $[F_3C—SO_2—N—CO—CF_3]^-$, $[F_3C—CO—N—CO—CF_3]^-$ and those in which the radicals $R^g$ to $R^l$ are each, independently of one another, methyl, ethyl, propyl, butyl, phenyl, trichloromethyl, dichloromethyl, chloromethyl, trifluoromethyl, difluoromethyl or fluoromethyl.

If the anion $A^{a-}$ is a methide (Vh)

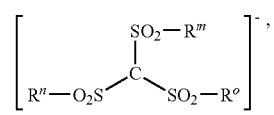

the radicals $R^m$ to $R^o$ are preferably each, independently of one another, trifluoromethyl, pentafluoroethyl, phenyl, trichloromethyl, dichloromethyl, chloromethyl, trifluoromethyl, difluoromethyl, fluoromethyl or unbranched or branched $C_1$-$C_{12}$-alkyl such as methyl, ethyl, 1-propyl, 2-propyl, 1-butyl, 2-butyl, 2-methyl-1-propyl(isobutyl), 2-methyl-2-propyl(tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, nonyl, decyl, undecyl or dodecyl. Particularly preferred methides (Vh) are $[(F_3C—SO_2)_3C]^-$ (tris(trifluoromethylsulfonyl)methide), $[(F_5C_2—SO_2)_3C]^-$ (bis(pentafluoroethylsulfonyl)methide) and those in which the radicals $R^m$ to $R^o$ are each, independently of one another, methyl, ethyl, propyl, butyl, phenyl, trichloromethyl, dichloromethyl, chloromethyl, trifluoromethyl, difluoromethyl or fluoromethyl.

If the anion $A^{a-}$ is an organic sulfate (Vi) $[R^pO—SO_3]^-$, the radical $R^p$ is preferably a branched or unbranched $C_1$-$C_{30}$-alkyl radical and particularly preferably methylsulfate, ethylsulfate, propylsulfate, butylsulfate, pentylsulfate, hexylsulfate, heptylsulfate or octylsulfate.

If the anion $A^{a-}$ is a halometalate (Vj) $[M_qHal_r]^{s-}$, M is preferably aluminum, zinc, iron, cobalt, antimony or tin. Hal is preferably chlorine or bromine, very particularly preferably chlorine. q is preferably 1, 2 or 3 and r and s are determined by the stoichiometry and charge on the metal ion.

The process of the present invention is very particularly preferably used to prepare a purified 1,3-substituted imidazolium salt (I) whose anion $A^{a-}$ is tetrafluoroborate, hexafluorophosphate, trifluoromethanesulfonate, methanesulfonate, formate, acetate, mandelate, nitrate, nitrite, trifluoroacetate, sulfate, hydrogensulfate, methylsulfate, ethylsulfate, propylsulfate, butylsulfate, pentylsulfate, hexylsulfate, heptylsulfate, octylsulfate, phosphate, dihydrogenphosphate, hydrogenphosphate, propionate, tetrachlorooaluminate, $Al_2Cl_7^-$, chlorozincate, chloroferrate, bis(trifluoromethylsulfonyl)imide(triflimide), bis(pentafluoroethylsulfonyl)imide, tris(trifluoromethylsulfonyl)methide(methide), bis(pentafluoroethylsulfonyl)methide, p-toluenesulfonate(tosylate), bis[salicylato(2-)]borate, tetracarbonylcobaltate, dimethylene glycol monomethyl ether sulfate, oleate, stearate, acrylate, methacrylate, maleate, hydrogencitrate, vinyl phosphonate, bis(pentafluoroethyl)phosphinate, bis[oxalato(2-)]borate, bis[1,2-benzenediolato(2-)-O,O']borate, dicyanamide, tris(pentafluoroethyl)trifluorophosphate, tris(heptafluoropropyl)trifluorophosphate, tetracyanoborate or chlorocobaltate.

The purified 1,3-substituted imidazolium salt (I) prepared in the process of the present invention is very particularly preferably the tetrafluoroborate, hexafluorophosphate, trifluoromethanesulfonate, methanesulfonate, formate, acetate, trifluoroacetate, sulfate, hydrogensulfate, methylsulfate, ethylsulfate, propylsulfate, butylsulfate, pentylsulfate, hexylsulfate, heptylsulfate, octylsulfate, phosphate, dihydrogenphosphate, hydrogenphosphate, propionate, tetrachlorooaluminate, $Al_2Cl_7^-$, chlorozincate, chloroferrate, bis(trifluoromethylsulfonyl)imide, bis(pentafluoroethylsulfonyl)imide, tris(trifluoromethylsulfonyl)methide, bis(pentafluoroethylsulfonyl)methide, p-toluenesulfonate of 1,3-dimethylimdazolium, 1-ethyl-3-methylimidazolium or 1-butyl-3-methylimidazolium.

The 1,3-substituted imidazolium salt (II) to be used in the process of the present invention comprises the 1,3-substituted imidazolium cation (Ia) as defined above which is identical to the 1,3-substituted imidazolium cation (Ia) of the purified 1,3-substituted imidazolium salt (I) to be prepared and the anion $Y^{y-}$ which is a partly or fully deprotonated anion of an inorganic or organic protic acid $H_yY$ (IV), where y is a positive integer and indicates the charge on the anion. Possible anions $Y^{y-}$ are in principle all partly or fully deprotonated anions of inorganic or organic protic acids which form salts with the 1,3-substituted imidazolium cation (Ia). $Y^{y-}$ is preferably a partly or fully deprotonated anion of an inorganic or organic protic acid as described in the definition of the anion $A^{a-}$ or chloride, bromide or iodide.

Particular preference is given to using a 1,3-substituted imidazolium salt (II) comprising chloride, bromide, methanesulfonate, hydrogencarbonate, carbonate, hydrogensulfate, diethylphosphate, tosylate or methylsulfate as anion $Y^{y-}$ in the process of the present invention.

The 1,3-substituted imidazolium salt (II) to be used is obtainable, for example, by means of generally known syntheses, for instance by alkylation of the corresponding 1-substituted imidazole.

As strong bases, it is in principle possible to use all bases which are able, under the given reaction conditions such as pressure and temperature, to convert the 1,3-substituted imidazolium salt (II) used into the corresponding 1,3-substituted imidazol-2-ylidene in the process of the present invention. Examples of suitable strong bases are alkoxides such as the alkali metal and alkaline earth metal salts of aliphatic alcohols, hydroxides such as the alkali metal and alkaline earth metal hydroxides (e.g. sodium, potassium or calcium hydroxide and their crown ether complexes, oxides such gaseous protic acid $H_aA$ (III) and the condensed, purified 1,3-substituted imidazolium salt (I) is isolated. Contacting can be carried out, for example, in a distillation column or a preferably packed residence section. The 1,3-substituted imidazol-2-ylidene which has been distilled off and the protic acid $H_aA$ (III) are preferably brought into contact with one another in countercurrent, with the purified 1,3-substituted imidazolium salt (I) formed being condensed as a result of its high boiling point and conveyed downward, so that the purified 1,3-substituted imidazolium salt (I) can be obtained directly as desired end product. Reaction apparatuses suitable for this purpose are apparatuses in general in which two gas streams can be mixed or brought into contact, for example distillation columns or tube reactors.

In another preferred variant, the 1,3-substituted imidazol-2-ylidene which has been distilled off is passed in the gaseous state into a receiver comprising the protic acid $H_aA$ (III) and the purified 1,3-substituted imidazolium salt (I) is isolated therefrom. Examples of suitable apparatuses are stirred vessels having a gas inlet device, stirred vessels provided with column, condenser and receiver. In general, it is advantageous to cool the receiver in order to counter vaporization of the protic acid (III) present in it. The gaseous 1,3-substituted imidazol-2-ylidene can be, for example, the gaseous overhead product from a distillation column or the gaseous stream directly from the apparatus in which the formation of the 1,3-substituted imidazol-2-ylidene occurs. In general, the protic acid (III) is used in a stoichiometric or superstoichiometric amount based on the 1,3-substituted imidazol-2-ylidene. Excess protic acid (III) is then removed in a simple manner by distillation or liquid/liquid extraction after the reaction, so that the purified 1,3-substituted imidazolium salt (I) can be obtained directly as desired end product.

In a further preferred variant, the 1,3-substituted imidazol-2-ylidene which has been distilled off is condensed in a condenser, the condensate is passed into a distillation receiver comprising the protic acid $H_aA$ (III) and the purified 1,3-substituted imidazolium salt (I) is isolated therefrom. Examples of suitable apparatuses are stirred vessels having a gas inlet device. In general, it is advantageous to cool the receiver in order to counter vaporization of the protic acid (III) present in it. In general, the protic acid (III) is used in a stoichiometric or superstoichiometric amount based on the 1,3-substituted imidazol-2-ylidene. Excess protic acid (III) is then removed in a simple manner by distillation or liquid/liquid extraction after the reaction, so that the purified 1,3-substituted imidazolium salt (I) can be obtained directly as desired end product.

The process of the present invention makes it possible to prepare the 1,3-substituted imidazolium salts (I) in particularly high purity. If the chloride, bromide or iodide salt is not wanted as purified 1,3-substituted imidazolium salt (I), the total concentration of chloride, bromide and iodide ions is preferably $\leq 100$ ppm by weight, particularly preferably $\leq 50$ ppm by weight, very particularly preferably $\leq 10$ ppm by weight and in particular $\leq 5$ ppm by weight. If purified 1,3-substituted imidazolium salt (I) having a metal-containing anion is not the desired product, the total metal concentration is preferably $\leq 100$ ppm by weight, particularly preferably $\leq 50$ ppm by weight, very particularly preferably $\leq 10$ ppm by weight and in particular $\leq 1$ ppm by weight. Here, the total metal concentration is the total concentration of metal which is present in bound or unbound, uncharged or ionic form in solution or suspension in the molten 1,3-substituted imidazolium salt (I).

The present invention provides a process for preparing purified 1,3-substituted imidazolium salts which has wide variability and flexibility in terms of the choice of substituents of the imidazolium cation and the choice of anion and leads, in a technically simple way, to high yields of pure to highly pure 1,3-substituted imidazolium salts. The process of the present invention can be carried out using 1,3-substituted imidazolium salts which have been prepared in any desired way. They can also comprise various impurities. The process of the present invention thus imposes no significant demands on the quality of the 1,3-substituted imidazolium salt used. As a result of the purification step via the gaseous 1,3-substituted imidazol-2-ylidene, the impurities originally present remain in the distillation vessel. The subsequent reaction of the 1,3-substituted imidazol-2-ylidene with the desired protic acid thus leads to a particularly pure product which is suitable without further purification for, for example, applications in the electronics sector ("electronic grade"). The direct reaction of the gaseous 1,3-substituted imidazol-2-ylidene with the desired protic acid or the introduction of the gaseous or condensed 1,3-substituted imidazol-2-ylidene into a receiver comprising the protic acid prevents or at least significantly reduces the formation of any by-products or decomposition products from the reactive 1,3-substituted imidazol-2-ylidene.

EXAMPLES

Comparative Example 1

7 g (0.04 mol) of [BMIM]Cl were mixed with 3.24 g (0.06 mol) of sodium methoxide, whereupon the mixture became slightly yellowish. The 1-butyl-3-methylimidazol-2-ylidene formed was subsequently distilled off under reduced pressure, going over at a temperature of about 70° C., and was collected in a distillation receiver which was cooled externally by means of dry ice. The distillate obtained was immediately analyzed by $^1$H and $^{13}$C NMR spectroscopy. No 1-butyl-3-methylimidazol-2-ylidene was able to be detected. The distillate consisted of decomposition products which were not identified further.

Example 2 (According to the Present Invention)

22 g (0.15 mol) of 1-ethyl-3-methylimidazolium chloride (hereinafter referred to as [EMIM]Cl for short) were mixed with 25.2 g (0.225 mol) of potassium tert-butoxide. The 1-ethyl-3-methylimidazol-2-ylidene formed was subsequently distilled off at a pressure of 40 Pa abs, going over at a temperature of 52-57° C., and was passed into a distillation receiver which contained 9.0 g (0.15 mol) of glacial acetic acid (concentrated acetic acid) and was cooled by means of ice water. The temperature at the bottom was 72-100° C. When the condensed 1-ethyl-3-methylimidazol-2-ylidene dripped into the distillation receiver comprising the glacial acetic acid, an exothermic reaction could be observed. The mixture in the distillation receiver turned a yellowish-brown color. Together with the initially charged glacial acetic acid, a total of 21.7 g of distillate were obtained. The distillate obtained was analyzed by $^1$H and $^{13}$C NMR spectroscopy. The spectra displayed signals of [EMIM] acetate and of excess acetic acid and tert-butanol. After separating off the excess glacial acetic acid and tert-butanol at 80° C. under reduced pressure, 15.6 g of EMIM acetate were obtained. This corresponds to a yield of 61%.

Example 3 (According to the Present Invention)

22 g (0.15 mol) of molten [EMIM]Cl were mixed with 25.2 g (0.225 mol) of potassium tert-butoxide. The 1-ethyl-3-methylimidazol-2-ylidene formed was subsequently distilled off at a pressure of 40-200 Pa abs, going over at a temperature of 47-52° C., and was passed into a distillation receiver which contained 14.4 g (0.15 mol) of methanesulfonic acid and was cooled by means of ice water. The temperature at the bottom was from 75 to 110° C. When the condensed 1-ethyl-3-methylimidazol-2-ylidene dripped into the distillation receiver comprising the methanesulfonic acid, an exothermic reaction could be observed. The mixture in the distillation receiver turned a yellowish-brown color. Together with the initially charged methanesulfonic acid, a total of 28.4 g of distillate were obtained. The distillate obtained was analyzed by $^1$H and $^{13}$C NMR spectroscopy. According to NMR analysis, it was [EMIM] methanesulfonate. The yield was 91.8%.

Comparative Example 4

25 g (0.143 mol) of 1-butyl-3-methylimidazolium chloride (hereinafter referred to as [BMIM]Cl for short) were mixed with 24.1 g (0.215 mol) of potassium tert-butoxide, whereupon the mixture immediately turned orange-red. The 1-butyl-3-methylimidazol-2-ylidene formed was subsequently distilled off at a pressure of 20 Pa abs, going over at a temperature of 58-66° C. The temperature at the bottom was 85-93° C. 14.34 g of distillate were obtained and were immediately mixed with methanol after the distillation. The pH of the mixture was 12. The mixture obtained was immediately analyzed by 1H and 13C NMR spectroscopy. Neither 1-butyl-3-methylimidazol-2-ylidene nor the 1-butyl-3-methylimidazolium cation could be detected here. The major part of the mixture comprises decomposition products which were not identified further.

We claim:
1. A process for preparing purified 1,3-substituted imidazolium salts of the formula (I)

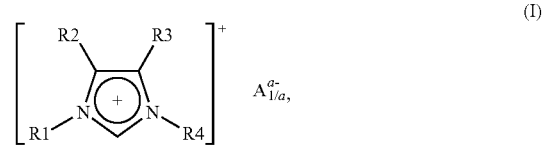

where
the radicals $R^1$, $R^2$, $R^3$ and $R^4$ are each, independently of one another, a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens, where adjacent radicals $R^1$ and $R^2$, $R^2$ and $R^3$ or $R^3$ and $R^4$ may also be joined to one another and the radicals $R^2$ and $R^3$ may each also be, independently of one another, hydrogen, halogen or a functional group;
and
$A^{a-}$ is the partly or fully deprotonated anion of an inorganic or organic protic acid $H_aA$ (III), where a is a positive integer and indicates the charge on the anion,
which comprises reacting a 1,3-substituted imidazolium salt of the formula (II),

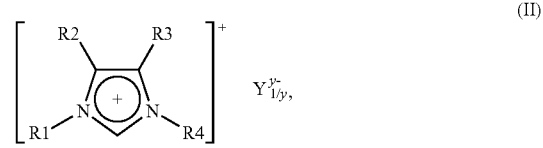

where the radicals $R^1$, $R^2$, $R^3$ and $R^4$ are as defined above and the anion $Y^{y-}$ is the partly or fully deprotonated anion of an inorganic or organic protic acid $$H_yY \quad (IV),$$

where y is a positive integer and indicates the charge on the anion, with a strong base at from 20 to 250° C. while distilling off the 1,3-substituted imidazol-2-ylidene formed, wherein the 1,3-substituted imidazol-2-ylidene which has been distilled off is brought into contact in the gaseous state with the protic acid $$H_aA \quad (III)$$

and/or the 1,3-substituted imidazol-2-ylidene which has been distilled off is passed in the gaseous or condensed state into a receiver comprising the protic acid $H_aA$ (III).

2. The process according to claim 1, wherein the radials $R^1$ and $R^4$ are each, independently of one another, methyl, ethyl, 1-propyl, 2-propyl, 1-butyl, 1-pentyl, 1-hexyl, 1-heptyl, 1-octyl, 1-nonyl, 1-decyl, 1-dodecyl, 1-tetradecyl, 1-hexadecyl, 1-octadecyl, 1-(2-ethyl)hexyl, benzyl, 3-phenylpropyl, 6-hydroxyhexyl or phenyl and the radicals $R^2$ and $R^3$ are each, independently of one another, hydrogen, methyl, ethyl, n-propyl, 2-propyl, 1-butyl, 1-hexyl, 6-hydroxyhexyl, phenyl or chlorine.

3. The process according to claim 1, wherein the anion $A^{a-}$ is fluoride; hexafluorophosphate; hexafluoroarsenate; hexafluoroantimonate; trifluoroarsenate; nitrite; nitrate; sulfate; hydrogensulfate; carbonate; hydrogencarbonate; phosphate; hydrogenphosphate; dihydrogenphosphate; vinyl phosphonate; dicyanamide; bis(pentafluoroethyl)phosphinate; tris(pentafluoroethyl)trifluorophosphate; tris(heptafluoropropyl)trifluorophosphate; bis[oxalato(2-)]borate; bis[salicylato(2-)]borate; bis[1,2-benzenediolato(2-)O,O'] borate; tetracyanoborate; tetracarbonylcobaltate;

tetrasubstituted borate of the formula (Va) $[BR^aR^bR^cR^d]^-$, where $R^a$ to $R^d$ are each, independently of one another, fluorine or a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens;

organic sulfonate of the formula (Vb) $[R^e—SO_3]^-$, where $R^e$ is a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens; carboxylate of the formula (Vc)

where $R^f$ is hydrogen or a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens; (fluoroalkyl) fluorophosphates of the formula (Vd)

where $1 \leq x \leq 6$, $1 \leq y \leq 8$ and $0 \leq z \leq 2y+1$;
imide of the formula (Ve), (Vf) or (IVg)

$$[R^g—SO_2—N—SO_2—R^h]^- \quad (Ve),$$

$$[R^i—SO_2—N—CO—R^j]^- \quad (Vf) \text{ or}$$

$$[R^k—CO—N—CO—R^l]^- \quad (IVg),$$

where $R^g$ to $R^l$ are each, independently of one another, hydrogen or a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens; methide of the formula (Vh)

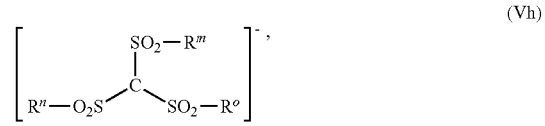

where $R^m$ to $R^o$ are each, independently of one another, hydrogen or a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens;

organic sulfate of the formula (Vi) $[R^pO—SO_3]^-$, where $R^p$ is a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogens; or halometalate of the formula (Vj) $[M_qHal_r]^{s-}$, where M is a metal and Hal is fluorine, chlorine, bromine or iodine, q and r are positive integers and indicate the stoichiometry of the complex and s is a positive integer and indicates the charge on the complex.

4. The process according to claim 3, wherein the radials $R^1$ and $R^4$ are each, independently of one another, methyl, ethyl, 1-propyl, 2-propyl, 1-butyl, 1-pentyl, 1-hexyl, 1-heptyl, 1-octyl, 1-nonyl, 1-decyl, 1-dodecyl, 1-tetradecyl, 1-hexadecyl, 1-octadecyl, 1-(2-ethyl)hexyl, benzyl, 3-phenylpropyl, 6-hydroxyhexyl or phenyl and the radicals $R^2$ and $R^3$ are each, independently of one another, hydrogen, methyl, ethyl, n-propyl, 2-propyl, 1-butyl, 1-hexyl, 6-hydroxyhexyl, phenyl or chlorine.

5. The process according to claim 1, wherein the anion $A^{a-}$ is tetrafluoroborate, hexafluorophosphate, trifluoromethanesulfonate, methanesulfonate, formate, acetate, mandelate, nitrate, nitrite, trifluoroacetate, sulfate, hydrogensulfate, methyl sulfate, ethyl sulfate, propyl sulfate, butyl sulfate, pentyl sulfate, hexyl sulfate, heptyl sulfate, octyl sulfate, phosphate, dihydrogenphosphate, hydrogenphosphate, propionate, tetrachloroaluminate, $Al_2Cl_7^-$, chlorozincate, chloroferrate, bis(trifluoromethylsulfonyl)imide, bis(pentafluoroethylsulfonyl)imide, tris(trifluoromethylsulfonyl)methide, bis(pentafluoroethylsulfonyl)methide, p-toluenesulfonate, bis[salicylato(2-)]borate, tetracarbonylcobaltate, dimethylene glycol monomethyl ether sulfate, octyl sulfate, oleate, stearate, acrylate, methacrylate, maleate, hydrogencitrate, vinyl phosphonate, bis(pentafluoroethyl)phosphinate, bis[oxalato(2-)]borate, bis[1,2-benzenediolato(2-)O,O']borate, dicyanamide, tris(pentafluoroethyl)trifluorophosphate, tris(heptafluoropropyl)trifluorophosphate, tetracyanoborate or chlorocobaltate.

6. The process according to claim 4, wherein the anion $A^{a-}$ is tetrafluoroborate, hexafluorophosphate, trifluoromethanesulfonate, methanesulfonate, formate, acetate, mandelate, nitrate, nitrite, trifluoroacetate, sulfate, hydrogensulfate, methyl sulfate, ethyl sulfate, propyl sulfate, butyl sulfate, pentyl sulfate, hexyl sulfate, heptyl sulfate, octyl sulfate, phosphate, dihydrogenphosphate, hydrogenphosphate, propionate, tetrachloroaluminate, $Al_2Cl_7^-$, chlorozincate, chloroferrate, bis(trifluoromethylsulfonyl)imide, bis(pentafluoroethylsulfonyl)imide, tris(trifluoromethylsulfonyl)methide, bis(pentafluoroethylsulfonyl)methide, p-toluenesulfonate, bis[salicylato(2-)]borate, tetracarbonylcobaltate, dimethylene glycol monomethyl ether sulfate, octyl sulfate, oleate, stearate, acrylate, methacrylate, maleate, hydrogencitrate, vinyl phosphonate, bis(pentafluoroethyl)phosphinate, bis[oxalato(2-)]borate, bis[1,2-benzenediolato(2-)O,O']borate, dicyanamide, tris(pentafluoroethyl)trifluorophosphate, tris(heptafluoropropyl)trifluorophosphate, tetracyanoborate or chlorocobaltate.

7. The process according to claim 1, wherein the anion $Y^{y-}$ is chloride, bromide, methanesulfonate, hydrogencarbonate, carbonate, hydrogensulfate, diethylphosphate, tosylate or methyl sulfate.

8. The process according to claim 6, wherein the anion $Y^{y-}$ is chloride, bromide, methanesulfonate, hydrogencarbonate, carbonate, hydrogensulfate, diethylphosphate, tosylate or methyl sulfate.

9. The process according to claim 1, wherein the 1,3-substituted imidazol-2-ylidene which has been distilled off is brought into contact in the gaseous state with gaseous protic acid $H_aA$ (III) and the condensed, purified 1,3-substituted imidazolium salt (I) is isolated.

10. The process according to claim 8, wherein the 1,3-substituted imidazol-2-ylidene which has been distilled off is passed in the gaseous state into a receiver comprising the protic acid $H_aA$ (III) and the purified 1,3-substituted imidazolium salt (I) is isolated therefrom.

11. The process according to claim 1, wherein the 1,3-substituted imidazol-2-ylidene which has been distilled off is condensed in a condenser, passed in the condensed state into a distillation receiver comprising the protic acid $H_aA$ (III) and the purified 1,3-substituted imidazolium salt (I) is isolated therefrom.

12. The process according to claim 10, wherein the 1,3-substituted imidazol-2-ylidene which has been distilled off is condensed in a condenser, passed in the condensed state into a distillation receiver comprising the protic acid $H_aA$ (III) and the purified 1,3-substituted imidazolium salt (I) is isolated therefrom.

13. The process according to claim 1, wherein the distillation is carried out at a pressure of from 0.0001 to 0.15 MPa abs.

14. The process according to claim 12, wherein the distillation is carried out at a pressure of from 0.0001 to 0.15 MPa abs.

* * * * *